(12) United States Patent
Xu et al.

(10) Patent No.: US 10,792,328 B2
(45) Date of Patent: Oct. 6, 2020

(54) NANOCOMPLEXES FOR DELIVERY OF SAPORIN

(71) Applicant: Trustees of Tufts College, Medford, MA (US)

(72) Inventors: Qiaobing Xu, Somerville, MA (US); Ming Wang, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 16/248,117

(22) Filed: Jan. 15, 2019

(65) Prior Publication Data

US 2019/0240288 A1     Aug. 8, 2019

Related U.S. Application Data

(63) Continuation of application No. 14/890,510, filed as application No. PCT/US2014/037859 on May 13, 2014, now abandoned.

(60) Provisional application No. 61/822,586, filed on May 13, 2013.

(51) Int. Cl.
| | |
|---|---|
| *A61K 38/16* | (2006.01) |
| *A61K 9/51* | (2006.01) |
| *A61K 47/54* | (2017.01) |
| *A61K 47/69* | (2017.01) |

(52) U.S. Cl.
CPC .......... *A61K 38/168* (2013.01); *A61K 9/5123* (2013.01); *A61K 47/543* (2017.08); *A61K 47/6929* (2017.08)

(58) Field of Classification Search
CPC . A61K 47/543; A61K 47/6929; A61K 9/5123
See application file for complete search history.

(56) References Cited

U.S. PATENT DOCUMENTS

| | | | |
|---|---|---|---|
| 5,679,350 A | 10/1997 | Jankun et al. | |
| 2009/0023673 A1 | 1/2009 | Manoharan et al. | |
| 2010/0226967 A1 * | 9/2010 | Low | A61K 47/6911 424/450 |
| 2012/0009222 A1 | 1/2012 | Nguyen et al. | |

FOREIGN PATENT DOCUMENTS

| | | | | |
|---|---|---|---|---|
| WO | WO-98/13007 A2 | | 4/1998 | |
| WO | WO-9813007 A2 * | | 4/1998 | ........... A61K 47/542 |
| WO | WO-2006/138380 A2 | | 12/2006 | |
| WO | WO-2006138380 A2 * | | 12/2006 | ........... C07D 295/12 |
| WO | WO-2010/053572 A2 | | 5/2010 | |
| WO | WO-2012/031205 A2 | | 3/2012 | |

OTHER PUBLICATIONS

Bergamaschi, G. et al. "Saporin, a ribosome-inactivating protein used to prepare immunotoxins, induces cell death via apoptosis" British Journal of Haematology, 1996, 93, 789-794 (Year: 1996).*
Bae, Y.H. et al. "Targeted drug delivery to tumors: Myths, reality and possibility" Journal of Controlled Release 153 (2011) 198-205 (Year: 2011).*
Wang, M. et al. "A Combinatorial Library of Unsaturated Lipidoids for Efficient Intracellular Gene Delivery" ACS Synth. Biol. 2012, 1, 403-407 (Year: 2012).*
Giansanti, F. et al. "Dissecting the Entry Route of Saporin-based a-CD7 Immunotoxins in Human T-Cell Acute Lymphoblastic Leukaemia Cells" Antibodies 2013, 2, 50-65 (Year: 2013).*
Hutchins, B.M. et al. "Selective Formation of Covalent Protein Heterodimers with an Unnatural Amino Acid" Chem Biol. Mar. 25, 2011; 18(3): 299-303 (Year: 2011).*
Akinc et al., "Development of lipidoid-siRNA formulations for systemic delivery to the liver," Molecular Therapy, 17(5):872-879 (2009).
Bae et al., "Targeted drug delivery to tumors: myths, reality and possibility," Journal of controlled release, 153(3):198-205 (2011).
Bergamaschi et al., "Saporin, a ribosome☐inactivating protein used to prepare immunotoxins, induces cell death via apoptosis," British journal of haematology, 93(4):789-794 (1996).
Giansanti et al., "Dissecting the Entry Route of Saporin-based a-CD7 Immunotoxins in Human T-Cell Acute Lymphoblastic Leukaemia Cells," Antibodies, 2(1):50-65 (2013).
Gonzalez-Toro et al., "Concurrent binding and delivery of proteins and lipophilic small molecules using polymeric nanogels," Journal of the American Chemical Society, 134(16):6964-6967 (2012).
Hutchins et al., "Selective formation of covalent protein heterodimers with an unnatural amino acid," Chemistry & biology, 18(3):299-303 (2011).
International Preliminary Report on Patentability for International Application No. PCT/US14/37859 dated Sep. 16, 2014.
International Search Report and Written Opinion for International Application No. PCT/US2014/037859 dated Sep. 16, 2014.
Place et al., "Formulation of small activating RNA into lipidoid nanoparticles inhibits xenograft prostate tumor growth by inducing p21 expression," Molecular Therapy—Nucleic Acids, 1:e15 (2012).
Wang et al., "A combinatorial library of unsaturated lipidoids for efficient intracellular gene delivery," ACS synthetic biology, 1(9):403-407 (2012).

* cited by examiner

*Primary Examiner* — Andrew S Rosenthal
(74) *Attorney, Agent, or Firm* — Dana M. Gordon; Foley Hoag LLP

(57) ABSTRACT

A nanocomplex, of particle size 50 nm to 1000 nm, containing saporin and a lipid-like compound, in which saporin binds to the lipid-like compound via non-covalent interaction or covalent bonding. The lipid-like compound has a hydrophilic moiety, a hydrophobic moiety, and a linker joining the hydrophilic moiety and the hydrophobic moiety. The hydrophilic moiety is optionally charged and the hydrophobic moiety has 8 to 24 carbon atoms. Also disclosed is a pharmaceutical composition containing such a nanocomplex and a pharmaceutically acceptable carrier. The nanocomplex is useful in treating diseases, such as cancer.

22 Claims, No Drawings

NANOCOMPLEXES FOR DELIVERY OF SAPORIN

CROSS REFERENCE TO RELATED APPLICATIONS

This application is a continuation of U.S. patent application Ser. No. 14/890,510, filed Nov. 11, 2015, which claims priority to International Application No. PCT/US2014/037859, filed May 13, 2014, which claims the benefit of priority to U.S. Provisional Application No. 61/822,586, filed on May 13, 2013.

BACKGROUND

Saporin, a ribosome inactivating protein extracted from the seeds of *Saponaria officinalis*, has medicinal use, e.g., treatment of cancer.

When used as a therapeutic agent, saporin must be delivered to its target cells. The low cell permeability of this protein makes it difficult to cross cell membranes to reach an intracellular target.

Target-specific vehicles have been used to deliver therapeutics. See Place et al., Molecular Therapy-Nucleic Acids, 1, e15 (2012). Examples include polymers and inorganic nanoparticles. See Gonzles-Toro et al., Journal of American Chemical Society, 134, 6964-67 (2012). However, these vehicles are often toxic or inefficient. See Akinc et al., Molecular Therapy, 17, 872-79 (2009).

There is a need to develop an efficient and safe vehicle for delivering saporin to its intracellular target.

SUMMARY

This invention is based on the discovery that lipid-like compounds are efficient and safe vehicles for use in delivery of saporin to cells.

In one aspect, this invention features a nanocomplex containing saporin (i.e., a therapeutic protein) and a lipid-like compound. The term "saporin" herein refers to the protein itself, a saporin conjugate, and a saporin derivative.

A saporin conjugate is a compound containing a saporin molecule chemically linked to one or more other molecules. Examples include, but are not limited to, a nucleoprotein, a glycoprotein, a phosphorprotein, a hemoglobin, and a lecithoprotein. A saporin derivative is a compound formed through hydrolysis of saporin, which results in slight alteration of saporin. Examples include, but are not limited to, a metaprotein, a proteose, and a peptide.

The lipid-like compound has a hydrophilic moiety, a hydrophobic moiety, and a linker joining the hydrophilic moiety and the hydrophobic moiety.

The hydrophilic moiety, optionally positively or negatively charged, can be an aliphatic or heteroaliphatic radical containing one or more hydrophilic groups and 1-20 carbon atoms. Examples of the hydrophilic group include, but are not limited to, amino, alkylamino, dialkylamino, trialkylamino, tetraalkylammonium, hydroxyamino, hydroxyl, carboxyl, carboxylate, carbamate, carbamide, carbonate, phosphate, phosphite, sulfate, sulfite, and thiosulfate.

Examples of the hydrophilic moiety include, but are not limited to, in which each of $R_a$, $R_a'$, $R_a''$, and $R_a'''$, independently, is a $C_1$-$C_{20}$ (e.g., $C_1$-$C_{10}$ and $C_1$-$C_6$) monovalent aliphatic radical, a $C_1$-$C_{20}$ (e.g., $C_1$-$C_{10}$ and $C_1$-$C_6$) monovalent heteroaliphatic radical, a monovalent aryl radical, or a monovalent heteroaryl radical; and Z is a $C_1$-$C_{20}$ (e.g., $C_1$-$C_{10}$ and $C_1$-$C_6$) bivalent aliphatic radical, a $C_1$-$C_{20}$ (e.g., $C_1$-$C_{10}$ and $C_1$-$C_6$) bivalent heteroaliphatic radical, a bivalent aryl radical, or a bivalent heteroaryl radical.

The hydrophobic moiety is a $C_{8-24}$ aliphatic radical or a $C_{8-24}$ heteroaliphatic radical (e.g., a $C_{8-24}$ heteroaliphatic radical containing one or more —S—S— groups, a $C_{12-20}$ aliphatic radical, a $C_{12-20}$ heteroaliphatic radical, a $C_{14-18}$ aliphatic radical, and a $C_{14-18}$ heteroaliphatic radical).

The linker can be O, S, Si, $C_1$-$C_6$ alkylene, in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical. Examples include, but are not limited to,

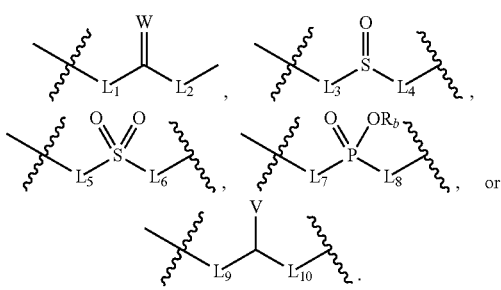

The lipid-like compound described above can be a compound of formula (I): $B_1$—$K_1$-A-$K_2$—$B_2$, in which A is the hydrophilic moiety, each of $B_1$ and $B_2$ is the hydrophobic moiety, and each of $K_1$ and $K_2$ is the linker.

The term "aliphatic" herein refers to a saturated or unsaturated, linear or branched, acyclic, cyclic, or polycyclic hydrocarbon moiety. Examples include, but are not limited to, alkyl, alkylene, alkenyl, alkenylene, alkynyl, alkynylene, cycloalkyl, cycloalkylene, cycloalkenyl, cycloalkenylene, cycloalkynyl, and cycloalkynylene moieties. The term "alkyl" or "alkylene" refers to a saturated, linear or branched hydrocarbon moiety, such as methyl, methylene, ethyl, ethylene, propyl, propylene, butyl, butylenes, pentyl, pentylene, hexyl, hexylene, heptyl, heptylene, octyl, octylene, nonyl, nonylene, decyl, decylene, undecyl, undecylene, dodecyl, dodecylene, tridecyl, tridecylene, tetradecyl, tetradecylene, pentadecyl, pentadecylene, hexadecyl, hexadecylene, heptadecyl, heptadecylene, octadecyl, octadecylene, nonadecyl, nonadecylene, icosyl, icosylene, triacontyl, and triacotylene. The term "alkenyl" or "alkenylene" refers to a linear or branched hydrocarbon moiety that contains at least one double bond, such as —CH=CH—CH$_3$ and —CH=CH—CH$_2$—. The term "alkynyl" or "alkynylene" refers to a linear or branched hydrocarbon moiety that contains at least one triple bond, such as —C≡C—CH$_3$ and —C≡C—CH$_2$—. The term "cycloalkyl" or "cycloalkylene" refers to a saturated, cyclic hydrocarbon moiety, such as cyclohexyl and cyclohexylene. The term "cycloalkenyl" or "cycloalkenylene" refers to a non-aromatic, cyclic hydrocarbon moiety that contains at least one double bond, such as cyclohexenyl cyclohexenylene. The term "cycloalkynyl" or "cycloalkynylene" refers to a non-aromatic, cyclic hydrocarbon moiety that contains at least one triple bond, cyclooctynyl and cyclooctynylene.

The term "heteroaliphatic" herein refers to an aliphatic moiety containing at least one heteroatom selected from N, O, P, B, S, Si, Sb, Al, Sn, As, Se, and Ge.

The term "oxyaliphatic" herein refers to an —O-aliphatic. Examples of oxyaliphatic include methoxy, ethoxy, n-propoxy, isopropoxy, n-butoxy, iso-butoxy, sec-butoxy, and tert-butoxy.

The term "aryl" herein refers to a $C_6$ monocyclic, $C_{10}$ bicyclic, $C_{14}$ tricyclic, $C_{20}$ tetracyclic, or $C_{24}$ pentacyclic aromatic ring system. Examples of aryl groups include, but are not limited to, phenyl, phenylene, naphthyl, naphthylene, anthracenyl, anthrcenylene, pyrenyl, and pyrenylene. The term "heteroaryl" herein refers to an aromatic 5-8 membered monocyclic, 8-12 membered bicyclic, 11-14 membered tricyclic, and 15-20 membered tetracyclic ring system having one or more heteroatoms (such as O, N, S, or Se). Examples of heteroaryl groups include, but are not limited to, furyl, furylene, fluorenyl, fluorenylene, pyrrolyl, pyrrolylene, thienyl, thienylene, oxazolyl, oxazolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolyl, isoquinolylene, indolyl, and indolylene.

Unless specified otherwise, aliphatic, heteroaliphatic, oxyaliphatic, alkyl, alkylene, alkenyl, alkenylene, alkynyl, alkynylene, cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl mentioned herein include both substituted and unsubstituted moieties. Possible substituents on cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on aliphatic, heteroaliphatic, oxyaliphatic, alkyl, alkylene, alkenyl, alkenylene, alkynyl, and alkynylene include all of the above-recited substituents except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl can also be fused with each other.

The lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Another aspect of this invention relates a pharmaceutical composition containing the nanocomplex described above and a pharmaceutically acceptable carrier. In this composition, the nanocomplex has a particle size of 50 to 500 nm (e.g., 50 to 300 nm and 50 to 180 nm); the pharmaceutical carrier is compatible with saporin, a lipid-like compound, and a nanocomplex contained in the composition (and preferably, capable of stabilizing the nanocomplex) and not deleterious to the subject to be treated.

The term "non-covalent interaction" refers to any non-covalent binding, which includes ionic interaction, hydrogen bonding, van der Waals interaction, and hydrophobic interaction.

The details of one or more embodiments of the invention are set forth in the description below. Other features, objects, and advantages of the invention will be apparent from the description and from the claims.

DETAILED DESCRIPTION

The nanocomplex of this invention contains a lipid-like compound having a hydrophilic moiety, a hydrophobic moiety, and a linker joining the hydrophilic moiety and the hydrophobic moiety.

The hydrophilic moiety contains one or more hydrophilic functional groups, e.g., hydroxyl, carbonyl, carboxyl, amino, sulfhydryl, phosphate, amide, ester, ether, carbamate, carbonate, carbamide, and phosphodiester. These groups can form hydrogen bonds and are optionally positively or negatively charged.

Examples of the hydrophilic moiety include, but are not limited to,

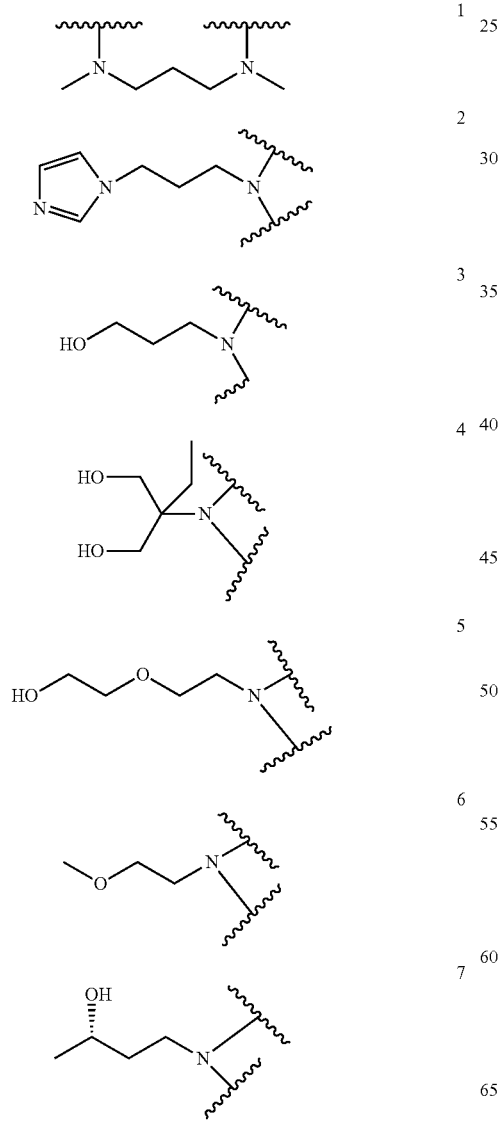

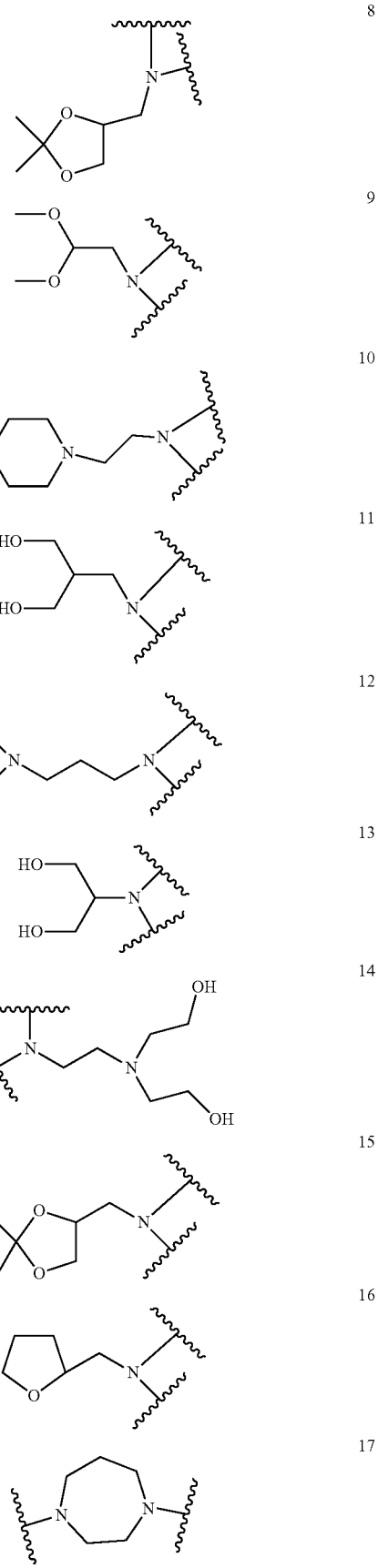

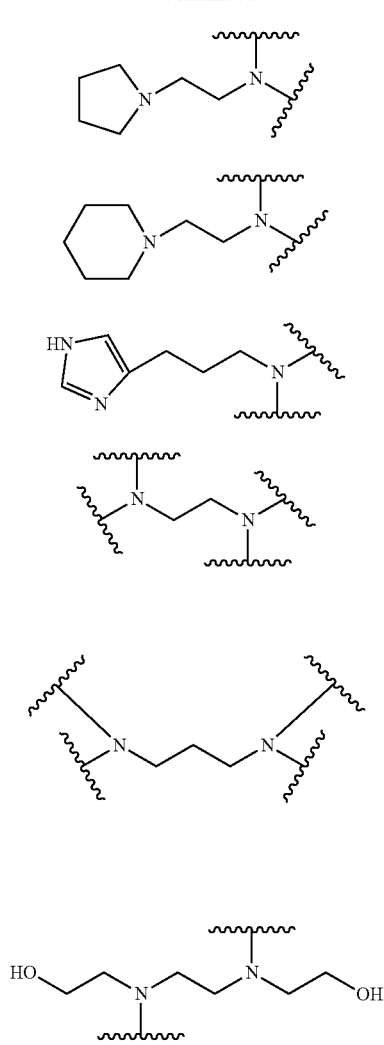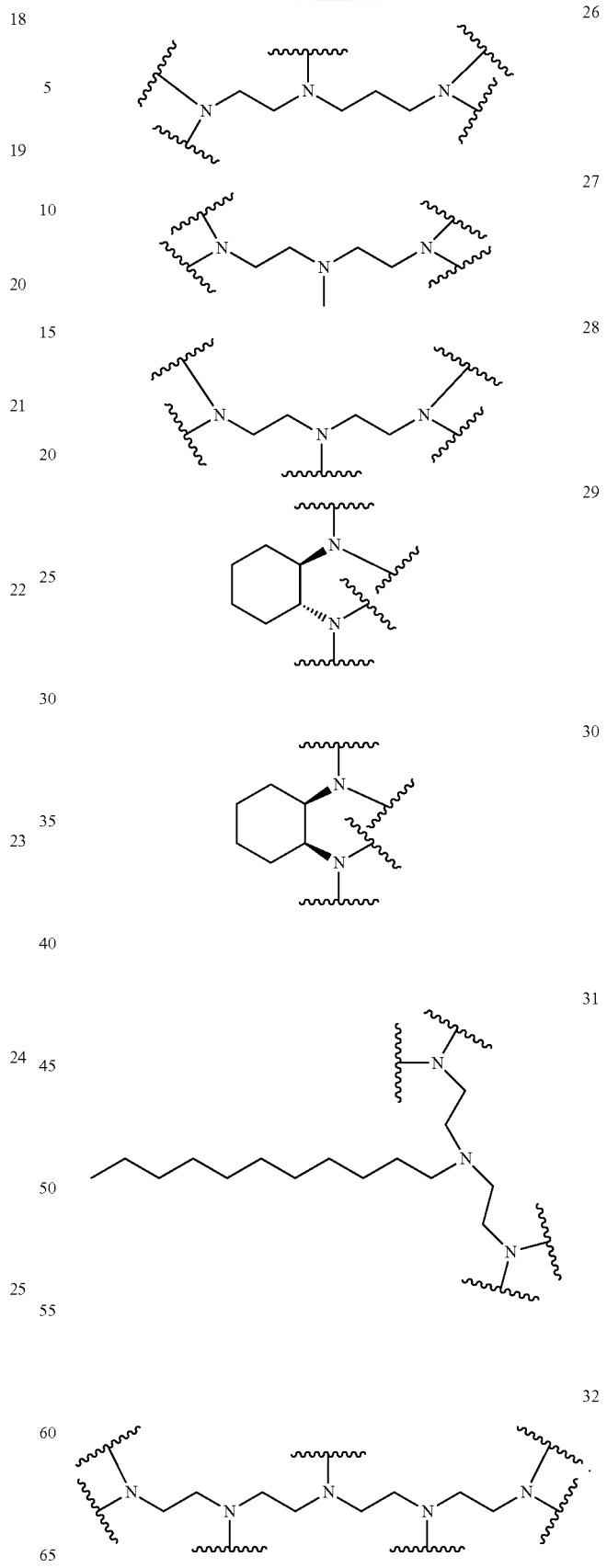

Other examples include those described in Akinc et al., Nature Biotechnology, 26, 561-69 (2008) and Mahon et al., US Patent Application Publication 2011/0293703.

The hydrophobic moiety is a saturated or unsaturated, linear or branched, acyclic or cyclic, aromatic or nonaromatic hydrocarbon moiety containing 8-24 carbon atoms. One or more of the carbon atoms can be replaced with a heteroatom, such as N, O, P, B, S, Si, Sb, Al, Sn, As, Se, and Ge. The hydrophobic moiety is optionally substituted with one or more groups described in the Summary section.

Examples include, but are not limited to,

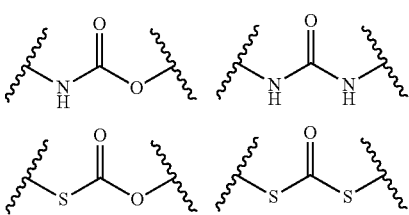

-continued

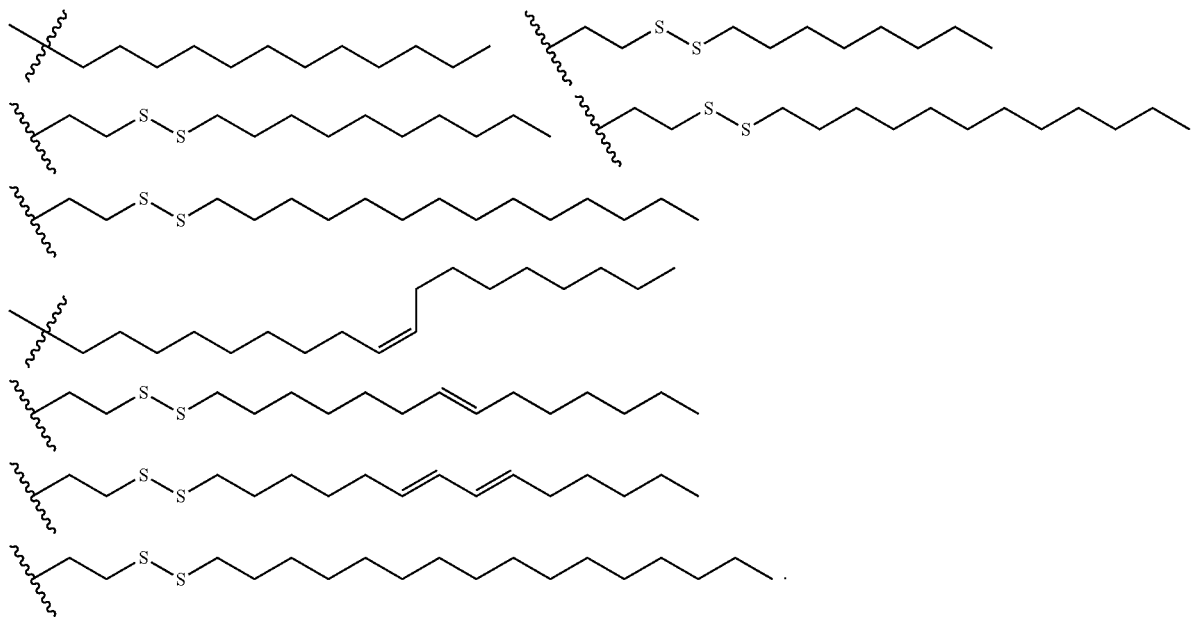

Turning to the linker(s), it links the hydrophilic moiety and the hydrophobic moiety. The linker can be any chemical group that is hydrophilic or hydrophobic, polar or non-polar, e.g., O, S, Si, amino, alkylene, ester, amide, carbamate, carbamide, carbonate, phosphate, phosphite, sulfate, sulfite, and thiosulfate. Examples include, but are not limited to,

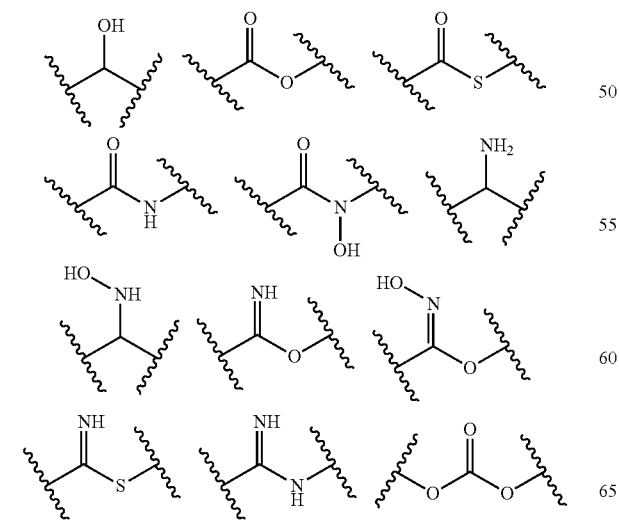

-continued

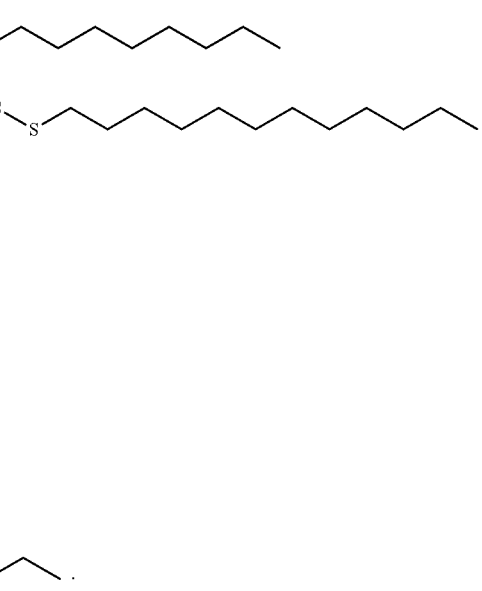

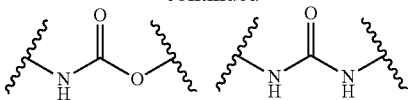

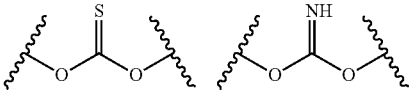

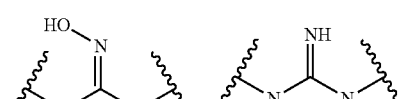

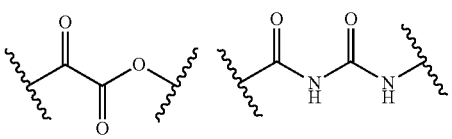

Shown below are exemplary lipid-like compounds useful for preparing the nanocomplex of this invention:
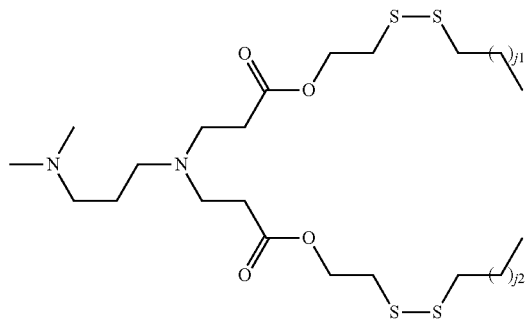
80-O14B, j1, j2 = 8;
80-O16B, j1, j2 = 10; and
80-O18B, j1, j2 = 12
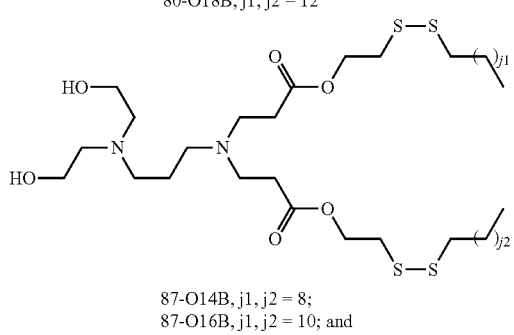
87-O14B, j1, j2 = 8;
87-O16B, j1, j2 = 10; and
87-O18B, j1, j2 = 12
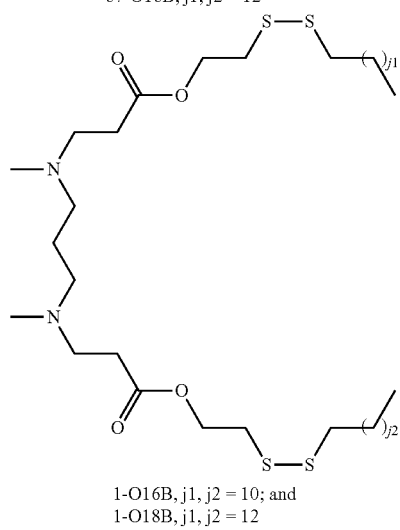
1-O16B, j1, j2 = 10; and
1-O18B, j1, j2 = 12
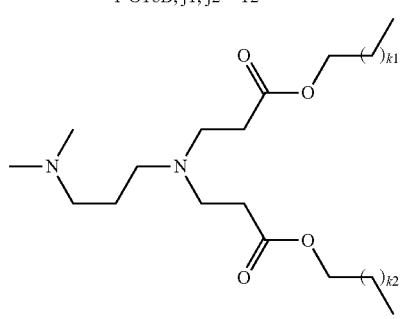
80-O14, k1, k2 = 12;
80-O16, k1, k2 = 14; and
80-O18, k1, k2 = 16.
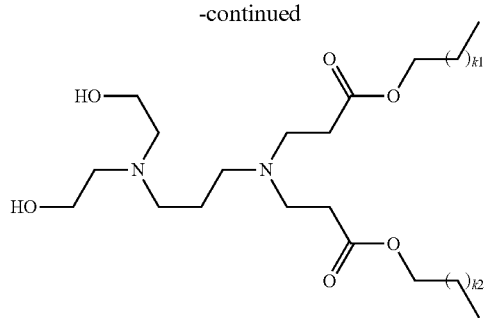
87-O14, k1, k2 = 12;
87-O16, k1, k2 = 14; and
87-O18, k1, k2 = 16.
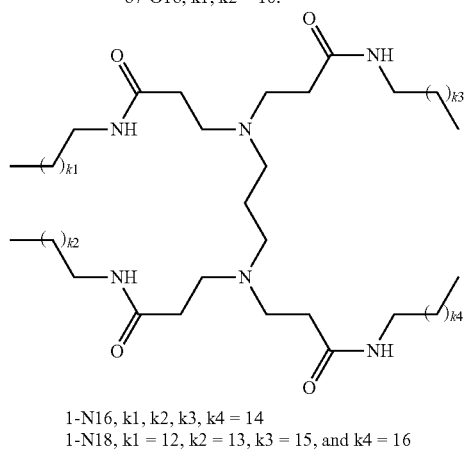
1-N16, k1, k2, k3, k4 = 14
1-N18, k1 = 12, k2 = 13, k3 = 15, and k4 = 16
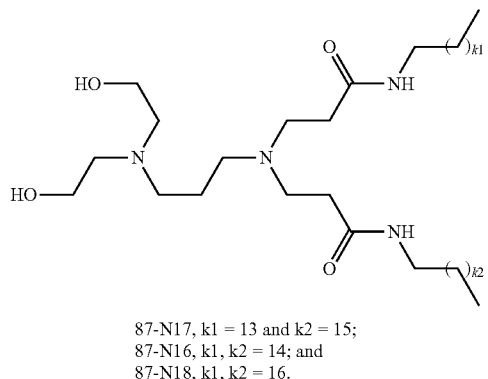
87-N17, k1 = 13 and k2 = 15;
87-N16, k1, k2 = 14; and
87-N18, k1, k2 = 16.
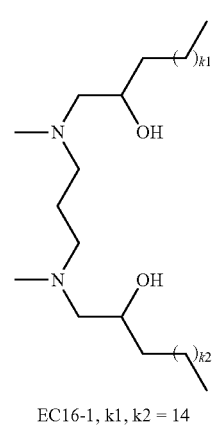
EC16-1, k1, k2 = 14

-continued

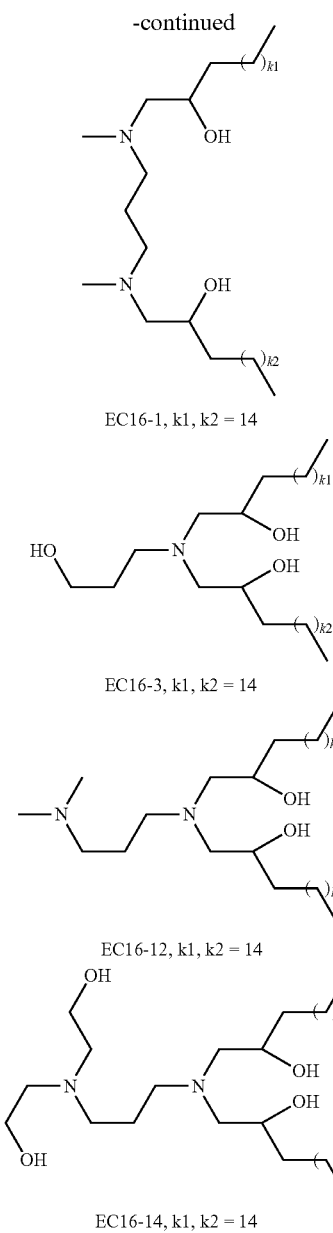

EC16-1, k1, k2 = 14

EC16-3, k1, k2 = 14

EC16-12, k1, k2 = 14

EC16-14, k1, k2 = 14

The lipid-like compounds can be prepared by methods well known in the art. See Wang et al., ACS Synthetic Biology, 1, 403-07 (2012); Manoharan, et al., International Patent Application Publication WO 2008/042973; and Zugates et al., U.S. Pat. No. 8,071,082.

The route shown below exemplifies synthesis of certain lipid-like compounds:

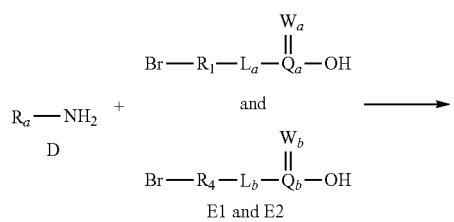

-continued

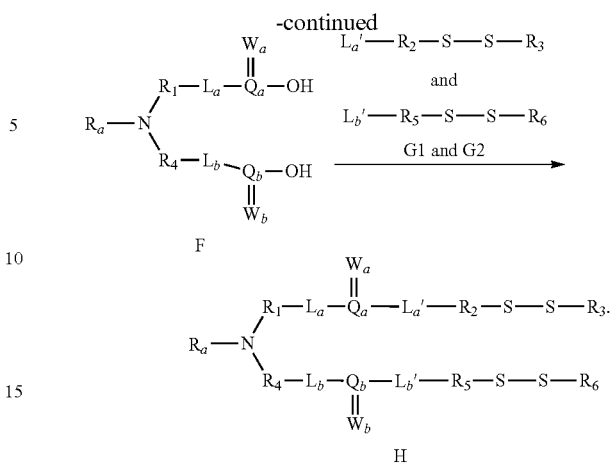

Each of $L_a$, $L_a'$, $L_b$, and $L_b'$ can be one of $L_1$-$L_{10}$; each of $W_a$ and $W_b$, independently, is W or V; and $R_a$ and $R_1$-$R_6$ are defined above, as well as $L_1$-$L_{10}$, W, and V.

In this exemplary synthetic route, an amine compound, i.e., compound D, reacts with bromides E1 and E2 to form compound F, which is then coupled with both G1 and G2 to afford the final product, i.e., compound H. One or both of the double bonds in this compound (shown above) can be reduced to one or two single bonds to obtain different lipid-like compounds of this invention.

Other lipid-like compounds contained in the nanocomplex of this invention can be prepared using other suitable starting materials through the above-described synthetic route and others known in the art. The method set forth above can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations, VCH Publishers (1989); T. W. Greene and P. G. M. Wuts, Protective Groups in Organic Synthesis, $2^{nd}$ Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

As mentioned above, these lipid-like compounds are useful for delivery of saporin. They can be preliminarily screened for their efficacy in delivering saporin by an in vitro assay and then confirmed by animal experiments and clinic trials. Other methods will also be apparent to those of ordinary skill in the art.

The above-described nanocomplexes can be prepared using procedures set forth in publications such as Wang et al., ACS Synthetic Biology, 1, 403-07 (2012). Generally, they are obtained by incubating saporin and a lipid-like compound in a buffer such as a sodium acetate buffer or a phosphate buffer. Typically, the ratio of saporin to a lipid-like compound is 100:1 to 1:1 by weight (e.g., 50:1 to 5:1 and 30:1 to 20:1). Saporin, commercially available, can be extracted from the seeds of *Saponaria officinalis* or overexpressed in and then purified from *Escherichia coli*. See Stirpe et al., Biochemical Journal, 216, 617-25 (1983); Fabbrini et al., Biochemical Journal, 322, 719-27 (1997); and Fabbrini et al., the FASEB Journal, 11, 1169-76 (1997).

Still within the scope of this invention is use of one of the above-described nanocomplexes for treating diseases, such as cancer, arthritis, neurodegenerative/cognitive disorders, an infection, chronic pain, and a sleeping disorder. Thus, this invention also relates to use of such a nonocomplex for treating these diseases by administering to a patient in need of the treatment an effective amount of a nanocomplex of this invention.

Further, this invention covers a method of administering an effective amount of the nanocomplex described above to a patient in need. "An effective amount" refers to the amount of nanocomplexes that is required to confer a therapeutic effect on the treated subject. Effective doses will vary, as recognized by those skilled in the art, depending on the types of diseases treated, route of administration, excipient usage, and the possibility of co-usage with other therapeutic treatment.

The nanocomplex is useful in treating cancers. Cancers that can be treated by the method of this invention include both solid and haematological tumours of various organs. Examples of solid tumors are pancreatic cancer; bladder cancer; colorectal cancer; breast cancer, including metastatic breast cancer; prostate cancer, including androgen-dependent and androgen-independent prostate cancer; renal cancer, including metastatic renal cell carcinoma; hepatocellular cancer; lung cancer, including non-small cell lung cancer (NSCLC), bronchioloalveolar carcinoma (BAC), and adenocarcinoma of the lung; ovarian cancer, including progressive epithelial or primary peritoneal cancer; cervical cancer; gastric cancer; esophageal cancer; head and neck cancer, including squamous cell carcinoma of the head and neck; melanoma; neuroendocrine cancer, including metastatic neuroendocrine tumors; brain tumors, including glioma, anaplastic oligodendroglioma, adult glioblastoma multiforme, and adult anaplastic astrocytoma; bone cancer; and soft tissue sarcoma. Examples of hematologic malignancy are acute myeloid leukemia; chronic myelogenous leukemia (CML), including accelerated CML and CML blast phase; acute lymphoblastic leukemia; chronic lymphocytic leukemia; Hodgkin's disease; non-Hodgkin's lymphoma, including follicular lymphoma and mantle cell lymphoma; B-cell lymphoma; T-cell lymphoma; multiple myeloma; Waldenstrom's macroglobulinemia; myelodysplastic syndromes, including refractory anemia, refractory anemia with ringed sideroblasts, refractory anemia with excess blasts (RAEB), and RAEB in transformation; and myeloproliferative syndromes.

To practice the method of the present invention, a composition having the above-described nanocomplexes can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having the nanocomplexes can also be administered in the form of suppositories for rectal administration.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1: Synthesis of Lipid-Like Compounds

Fourteen lipid-like compounds were prepared following the procedure described below.

In a 5-mL Teflon-lined glass screw-top vial, acrylate with disulfide bonds was added to amine at a molar ratio of 2.4:1. The mixture was stirred at 90° C. for two days. After cooling, the lipid-like compound thus formed was used without purification unless otherwise noted. Optionally, it was purified using flash chromatography on silica gel and characterized by proton nuclear magnetic resonance.

Following the above-described procedure, compound 80-O14B was prepared using N,N'-dimethylpropane-1,3-diamine and 2-(decyldisulfanyl)ethyl acrylate, which have the structures shown below:

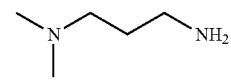

N,N'-dimethylpropane-1,3-diamine

-continued

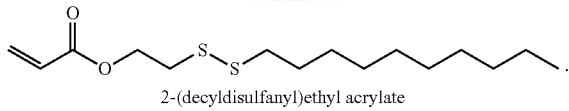
2-(decyldisulfanyl)ethyl acrylate

Example 2: Synthesis of Lipid-Like Compound 80-O16B

Compound 80-O16B was prepared following exactly the same procedure described in Example 1 except that 2-(dodecyldisulfanyl)ethyl acrylate (structure shown below) was used instead of 2-(decyldisulfanyl)ethyl acrylate.

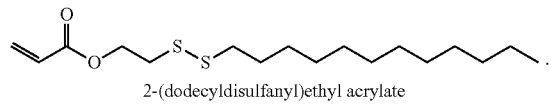 [SMILES: C=CC(=O)OCCSSCCCCCCCCCCCC]
2-(dodecyldisulfanyl)ethyl acrylate

Example 3: Synthesis of Lipid-Like Compound 80-O18B

Compound 80-O18B was prepared following exactly the same procedure described in Example 1 except that 2-(tetradecyldisulfanyl)ethyl acrylate (structure shown below) was used instead of 2-(decyldisulfanyl)ethyl acrylate.

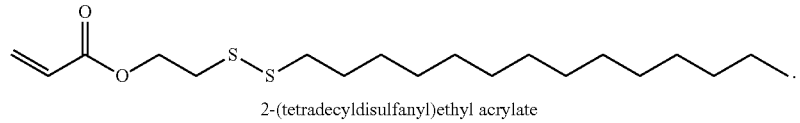 [SMILES: C=CC(=O)OCCSSCCCCCCCCCCCCCC]
2-(tetradecyldisulfanyl)ethyl acrylate

Example 4: Synthesis of Lipid-Like Compound 87-O14B

Compound 87-O14B was prepared following exactly the same procedure described in Example 1 except that 2,2'-(3-aminopropylazanediyl)diethanol (structure shown below) was used instead of N,N'-dimethylpropane-1,3-diamine.

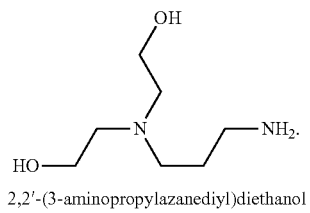 [SMILES: NCCCN(CCO)CCO]
2,2'-(3-aminopropylazanediyl)diethanol

Example 5: Synthesis of Lipid-Like Compound 87-O16B

Compound 87-O16B was prepared following exactly the same procedure described in Example 2 except that 2,2'-(3-aminopropylazanediyl)diethanol was used instead of N,N'-dimethylpropane-1,3-diamine.

Example 6: Synthesis of Lipid-Like Compound 87-O18B

Compound 87-O18B was prepared following exactly the same procedure described in Example 3 except that 2,2'-(3-aminopropylazanediyl)diethanol was used instead of N,N'-dimethylpropane-1,3-diamine.

Example 7: Synthesis of Lipid-Like Compound 1-O16B

Compound 1-O16B was prepared following exactly the same procedure described in Example 2 except that $N^1,N^3$-dimethylpropane-1,3-diamine (structure shown below) was used instead of N,N'-dimethylpropane-1,3-diamine.

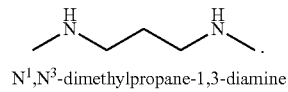
$N^1,N^3$-dimethylpropane-1,3-diamine

Example 8: Synthesis of Lipid-Like Compound 1-O18B

Compound 1-O18B was prepared following exactly the same procedure described in Example 7 except that 2-(tetradecyldisulfanyl)ethyl acrylate was used instead of 2-(dodecyldisulfanyl)ethyl acrylate.

Examples 9-14: Synthesis of Lipid Like Compounds 80-O14, 80-O16, 80-O18, 87-O14, 87-O16, and 87-O18

Compounds 80-O14, 80-O16, 80-O18, 87-O14, 87-O16, and 87-O18 were prepared using exactly the same method described in Examples 1-6, respectively, except that tetradecyl acrylate, hexadecyl acrylate, or octadecyl acrylate was used instead of a disulfanyl acrylate.

Examples 15-18: Synthesis of Lipid-Like Compounds EC16-1, EC16-3, EC16-12, and EC16-14

In a 5-mL Teflon-lined glass screw-top vial, 1,2-epoxyoctadecane was added to amine at a molar ratio of 2.4:1. The mixture was stirred at 90° C. for two days. After cooling, the lipid-like compound thus formed was used without purification unless otherwise noted. Optionally, it was purified using flash chromatography on silica gel and characterized by proton nuclear magnetic resonance.

Following the above-described procedure, compound EC16-1 was prepared using $N^1,N^3$-dimethylpropane-1,3-diamine; compound EC16-3 was prepared using 3-aminopropanol; compound E16-12 was prepared using N,N'-dimethylpropane-1,3-diamine; and EC16-14 was prepared using 2,2'-(3-aminopropylazanediyl)diethanol.

Examples 19-54: Preparation of Nanocomplex Compositions

The lipid-like compound prepared in one of Examples 1-18 was dissolved in sodium acetate solution (25 mM, pH=5.5) at a concentration of 1 mg/mL. Optionally, cholesterol and 1,2-dioleoyl-sn-glycero-3-phosphoethanolamine ("DOPE") were also included. Saporin was introduced to the resulting mixture, which was incubated for 15 minutes at room temperature. The weight ratio between the lipid-like compound and saporin was 6:1, 20:1, or 40:1. The nanocomplex composition thus prepared was subjected to the in vitro assay described in Example 55 below. Compositions 1-32 were prepared following the above-described procedure. See the table below for the weight ratios between lipid-like compounds, cholesterol, DOPE, and saporin. Note that also included in this table are the weight ratios for compositions 33-35 and a comparative composition, all of which were prepared following the procedure described below.

Compositions 33 and 34 were prepared using a thin film hydration method described below. Compound 1-O16B or 1-O18B, cholesterol, and DOPE were mixed at a weight ratio of 16:4:1 in chloroform, which was then evaporated under vacuum, leaving a thin film. Re-hydrating the thin film in PBS yielded a solution of 1-O16B or 1-O18B at a concentration of 1 mg/mL. Saporin was added (1-O16B or 1-O18B:saporin=15:1 by weight). The mixture was incubated for 15 minutes at room temperature followed by addition of mPEG2000-ceramide C16/DSPE-PEG2000-Biotin (purchased from Avanti Polar Lipids, weight/weight=8:1, PEG 10% by weight of 1-O16B, this compo- nent not shown in the table above). The mixture was again incubated for 15 minutes to yield a nanocomplex composition, Composition 33 or 34. See the table below for the weight ratios between Compound 1-O16B or 1-O18B, cholesterol, DOPE, and saporin. These two compositions were subjected to the in vivo assay described in Example 55 below.

Composition 35 was prepared according to the following procedure. EC16-1 was dissolved in a phosphate buffer solution (25 mM, pH=7.4). Saporin was introduced to the resulting mixture, which was incubated for 15 minutes at room temperature. The weight ratio between EC16-1 and saporin was 20:1. A comparative composition was prepared following the same procedure described above except that RNase was used instead of saporin and the weight ratio between EC16-1 and RNase was 6:5. These two nanocomplex compositions were also subjected to the in vitro assay described in Example 55 below.

| Composition No. | Composition by weight |
|---|---|
| 1 | 80-O14B (16 μg), cholesterol (8 μg), DOPE (1 μg), and saporin (0.8 μg) |
| 2 | 80-O14 (16 μg), cholesterol (8 μg), DOPE (1 μg), and saporin (0.8 μg) |
| 3 | 80-O16B (16 μg), cholesterol (8 μg), DOPE (1 μg), and saporin (0.8 μg) |
| 4 | 80-O16 (16 μg), cholesterol (8 μg), DOPE (1 μg), and saporin (0.8 μg) |
| 5 | 80-O18B (16 μg), cholesterol (8 μg), DOPE (1 μg), and saporin (0.8 μg) |
| 6 | 80-O18 (16 μg), cholesterol (8 μg), DOPE (1 μg), and saporin (0.8 μg) |
| 7 | 87-O16B (16 μg), cholesterol (8 μg), DOPE (1 μg), and saporin (0.8 μg) |
| 8 | 87-O16 (16 μg), cholesterol (8 μg), DOPE (1 μg), and saporin (0.8 μg) |
| 9 | 80-O14B (16 μg), cholesterol (8 μg), DOPE (1 μg), and saporin (0.4 μg) |
| 10 | 80-O14 (16 μg), cholesterol (8 μg), DOPE (1 μg), and saporin (0.4 μg) |
| 11 | 80-O16B (16 μg), cholesterol (8 μg), DOPE (1 μg), and saporin (0.4 μg) |
| 12 | 80-O16 (16 μg), cholesterol (8 μg), DOPE (1 μg), and saporin (0.4 μg) |
| 13 | 80-O18B (16 μg), cholesterol (8 μg), DOPE (1 μg), and saporin (0.4 μg) |
| 14 | 80-O18 (16 μg), cholesterol (8 μg), DOPE (1 μg), and saporin (0.4 μg) |
| 15 | 87-O16B (16 μg), cholesterol (8 μg), DOPE (1 μg), and saporin (0.4 μg) |
| 16 | 87-O16 (16 μg), cholesterol (8 μg), DOPE (1 μg), and saporin (0.4 μg) |
| 17 | 80-O14B (8 μg), cholesterol (4 μg), DOPE (1 μg), and saporin (0.4 μg) |
| 18 | 80-O14 (8 μg), cholesterol (4 μg), DOPE (1 μg), and saporin (0.4 μg) |
| 19 | 80-O16B (8 μg), cholesterol (4 μg), DOPE (1 μg), and saporin (0.4 μg) |
| 20 | 80-O16 (8 μg), cholesterol (4 μg), DOPE (1 μg), and saporin (0.4 μg) |
| 21 | 80-O18B (8 μg), cholesterol (4 μg), DOPE (1 μg), and saporin (0.4 μg) |
| 22 | 80-O18 (8 μg), cholesterol (4 μg), DOPE (1 μg), and saporin (0.4 μg) |
| 23 | 87-O16B (8 μg), cholesterol (4 μg), DOPE (1 μg), and saporin (0.4 μg) |
| 24 | 87-O16 (8 μg), cholesterol (4 μg), DOPE (1 μg), and saporin (0.4 μg) |
| 25 | 80-O14B (8 μg), cholesterol (4 μg), DOPE (1 μg), and saporin (0.2 μg) |
| 26 | 80-O14 (8 μg), cholesterol (4 μg), DOPE (1 μg), and saporin (0.2 μg) |
| 27 | 80-O16B (8 μg), cholesterol (4 μg), DOPE (1 μg), and saporin (0.2 μg) |
| 28 | 80-O16 (8 μg), cholesterol (4 μg), DOPE (1 μg), and saporin (0.2 μg) |
| 29 | 80-O18B (8 μg), cholesterol (4 μg), DOPE (1 μg), and saporin (0.2 μg) |
| 30 | 80-O18 (8 μg), cholesterol (4 μg), DOPE (1 μg), and saporin (0.2 μg) |
| 31 | 87-O16B (8 μg), cholesterol (4 μg), DOPE (1 μg), and saporin (0.2 μg) |
| 32 | 87-O16 (8 μg), cholesterol (4 μg), DOPE (1 μg), and saporin (0.2 μg) |
| 33 | 1-O16B (16 μg), cholesterol (4 μg), DOPE (1 μg), and saporin (1.07 μg) |
| 34 | 1-O18B (16 μg), cholesterol (4 μg), DOPE (1 μg), and saporin (1.07 μg) |
| 35 | EC16-1 (8 μg) and saporin (0.4 μg) |
| Comparative | EC16-1 (8 μg) and RNase (6.7 μg) |

Example 55: Evaluation of Saporin Delivery Efficiency

Compositions 1-32 were tested for delivery of saporin into cells MDA-MB-231.

Cell Culture

The two cells lines were purchased from ATCC (Manassas, Va.) and cultured in Dulbecco's Modified Eagle Medium ("DMEM") supplemented with 10% Fetal Bovine Serum ("FBS") and 1% penicillin/streptomycin at 37° C. in the presence of 5% $CO_2$. For the protein transfection assay described below, cells were seeded in 96-well plates at a density of 10,000 cells per well a day prior to transfection.

In Vitro Protein Transfection

To evaluate saporin delivery efficiency, lipid-like compound/saporin nanocomplexes prepared in Examples 19-54 were added to MDA-MB-231 cancer cells and incubated at 37° C. for 24 hours. The saporin concentration was 0.1 μg/250 μL in PBS. The same volume of PBS without any lipid-like compound or saporin was used as a control. The cell viability was determined by the Alamar Blue assay after 24 hours of incubation. All transfection studies were performed in quadruplicate.

Unexpectedly, lipid-like compounds 80-O14B, 80-O16B, 80-O18B, and 87-O16B, 80-O16, 80-O18, and 87-O16 demonstrated high saporin delivery efficiency under all four studied conditions.

More specifically, cells treated with Compositions 9 (containing 80-O14B), 10 (containing 80-O14), 11 (containing 80-O16B), 12 (containing 80-O16), 13 (containing 80-O18B), 14 (containing 80-O18), 15 (containing 87-O16B), and 16 (containing 87-O16) showed, respectively, cell viabilities of 32%, 80%, 9%, 57%, 12%, 51%, 39%, and 72%.

Composition 35 and the comparative composition were tested for delivery of saporin into murine melanoma cell line B16F10 following the same procedure described above except that B16F10 was used instead of MDA-MB-231. Cell viability was determined by the Alamar Blue assay after 24 hours of incubation. For the cells treated with composition 35 containing saporin nanocomplexes, their viability was 25%; and for the cells treated with the comparative composition containing RNase nanocomplexes, their viability was 100%. Unexpectedly, saporin nanocomplexes demonstrated high delivery efficiency. By contrast, RNase was not delivered to B16F10 cells by RNase nanocomplexes.

In Vivo Cancer Treatment

Composition 33 (i.e., 1-O16B/saporin) and Composition 34 (i.e., 1-O18B/saporin) were tested for in vivo inhibiting tumor growth following the procedure described below. More specifically, BALB/c mice bearing 4T1-12B breast tumors were developed from a 4T1-12B cell suspension in DMEM supplemented with 10% FBS at a concentration of $10^7$ cells/ml. An aliquot (100 μl) of the cell suspension was injected into the mammary fat pad of 4-6 week-old female BALB/c mice. The mice were sorted into four groups randomly (n=7 for treatment group, n=5 for control groups) seven days after the injection. The mice were injected through tail-vein every three days. For the treatment group, each mouse was injected with 5.5 mg/kg of 1-O16B or 1-O18B and 330 μg/kg of saporin. Tumor volumes were measured every three days.

PBS without 1-O16B, 1-O18B, and saporin was also injected as a control. Comparative studies were also conducted using saporin in PBS without 1-O16B and 1-O18B.

Unexpectedly, at Day 16, mice treated with Composition 31 or 32 had a tumor size of less than 100 mm³, much smaller than that for mice treated with PBS (i.e., 200 mm³) and those treated with saporin (i.e., more than 120 mm³); and at Day 22, mice treated with Composition 32 had a tumor size of 100 mm³, much smaller than that in mice treated with PBS or saporin (i.e., more than 250 mm³).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A nanocomplex comprising saporin and a lipid-like compound, wherein the nanocomplex has a particle size of 50 nm to 1000 nm; the saporin binds to the lipid-like compound via non-covalent interaction; and the lipid-like compound has a hydrophilic moiety, a hydrophobic moiety, and a linker joining the hydrophilic moiety and the hydrophobic moiety, wherein the hydrophobic moiety is a heteroaliphatic radical comprising one or more —S—S— groups and 8 to 24 carbon atoms;

the hydrophilic moiety is optionally charged, and is an aliphatic or heteroaliphatic radical comprising one or more hydrophilic groups and 1-20 carbon atoms, each of the hydrophilic groups being amino, alkylamino, dialkylamino, trialkylamino, tetraalkylammonium, hydroxyamino, hydroxyl, carboxyl, carboxylate, carbamate, carbamide, carbonate, phosphate, phosphite, sulfate, sulfite, or thiosulfate; and the linker is O, S, Si, C alkylene,

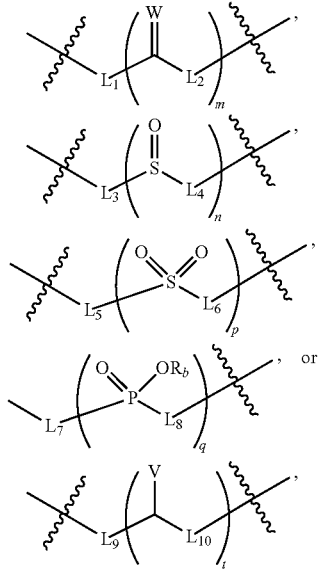

in which each of m, n, p, q, and t, independently, is 1-6; W is O, S, or $NR_c$; each of $L_1$, $L_3$, $L_5$, $L_7$, and $L_9$ independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

2. The nanocomplex of claim 1, wherein the hydrophilic moiety is

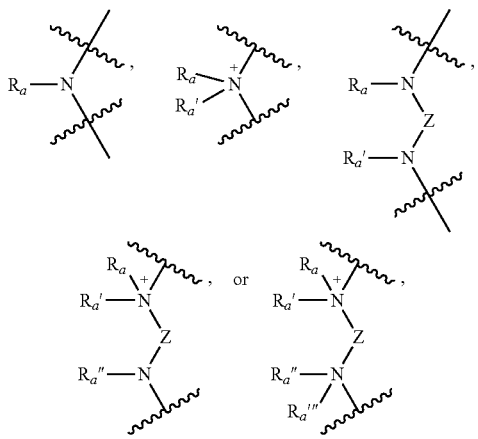

each of $R_a$, $R_a'$, $R_a''$, and $R_a'''$, independently, being a $C_1$-$C_{20}$ monovalent aliphatic radical, a $C_1$-$C_{20}$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical.

3. The nanocomplex of claim 2, wherein the hydrophobic moiety is a $C_{12-20}$ heteroaliphatic radical comprising one or more S—S— groups, and the linker is O, S, Si, $C_1$-$C_6$ alkylene,

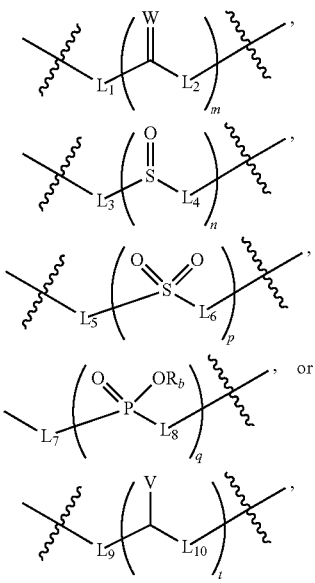

in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

4. The nanocomplex of claim 3, wherein the hydrophobic moiety is a $C_{14-18}$ heteroaliphatic radical comprising one or more —S—S— groups, and the linker is

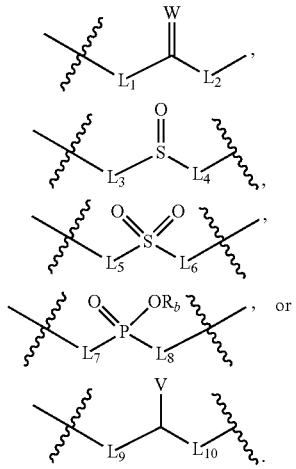

5. The nanocomplex of claim 2, wherein the hydrophilic moiety is

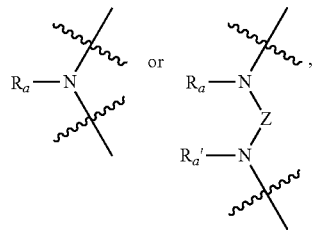

in which each of $R_a$ and $R_a'$, independently, is, H, a $C_1$-$C_{10}$ monovalent aliphatic radical, a $C_1$-$C_{10}$ monovalent heteroaliphatic radical, a monovalent aryl radical, or a monovalent heteroaryl radical; and Z is a $C_1$-$C_{10}$ bivalent aliphatic radical, a $C_1$-$C_{10}$ bivalent heteroaliphatic radical, a bivalent aryl radical, or a bivalent heteroaryl radical.

6. The nanocomplex of claim 5, wherein the hydrophobic moiety is a $C_{12-20}$ heteroaliphatic radical comprising one or more —S—S— groups, and the linker is O, S, Si, $C_1$-$C_6$ alkylene,

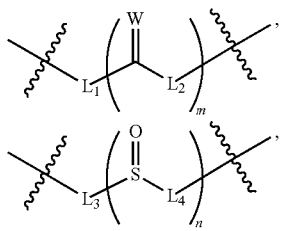

-continued

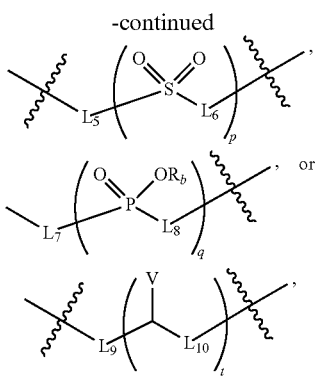

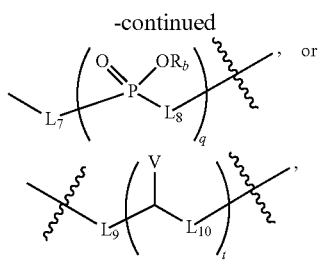

in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

7. The nanocomplex of claim 6, wherein the hydrophobic moiety is a $C_{14-18}$ heteroaliphatic radical comprising one or more —S—S— groups, and the linker is

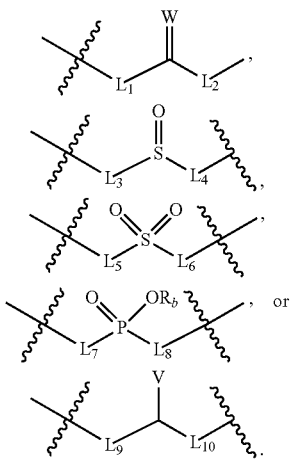

8. The nanocomplex of claim 1, wherein the linker is O, S, Si, $C_1$-$C_6$ alkylene,

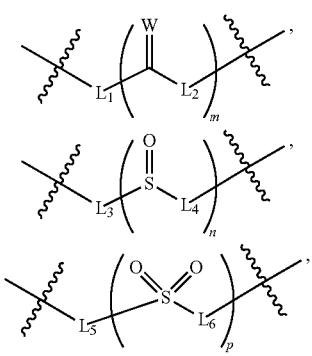

in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

9. The nanocomplex of claim 8, wherein the hydrophobic moiety is a $C_{12-20}$ heteroaliphatic radical comprising one or more —S—S— groups.

10. The nanocomplex of claim 9, wherein the hydrophobic moiety is a $C_{14-18}$ heteroaliphatic radical comprising one or more —S—S— groups.

11. The nanocomplex of claim 8, wherein the linker is

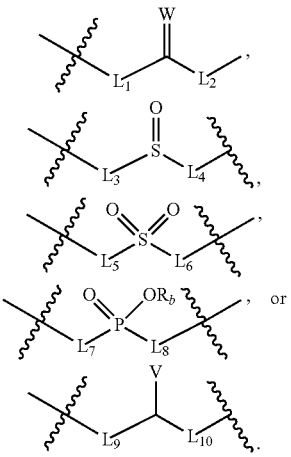

12. The nanocomplex of claim 11, wherein the hydrophobic moiety is a $C_{12-20}$ heteroaliphatic radical comprising one or more —S—S— groups.

13. The nanocomplex of claim 12, wherein the hydrophobic moiety is a $C_{14-18}$ heteroaliphatic radical comprising one or more —S—S— groups.

14. The nanocomplex of claim 1, wherein the hydrophobic moiety is a $C_{12-20}$ heteroaliphatic radical comprising one or more —S—S— groups.

15. The nanocomplex of claim 14, wherein the hydrophobic moiety is a $C_{14-18}$ heteroaliphatic radical comprising one or more —S—S— groups.

16. The nanocomplex of claim 1, wherein the lipid-like compound has additional one to three hydrophilic moieties, additional one to three hydrophobic moieties, and additional one to seven linkers.

17. The nanocomplex of claim 16, wherein the lipid-like compound is a compound of formula (I): $B_1$-$K_1$-A-$K_2$-$B_2$, in which A, the hydrophilic moiety, is

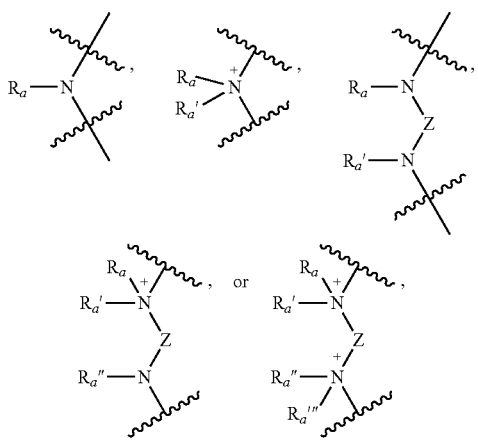

each of $R_a$, $R_a'$, $R_a''$, and $R_a'''$, independently, being a $C_1$-$C_{20}$ monovalent aliphatic radical, a $C_1$-$C_{20}$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical;

each of $B_1$, the hydrophobic moiety, and $B_2$, also the hydrophobic moiety, independently, is a $C_{12\text{-}20}$ aliphatic radical or a $C_{12}$-20 heteroaliphatic radical; and each of $K_1$, the linker, and $K_2$, also the linker, independently, is O, S, Si, $C_1$-$C_6$ alkylene,

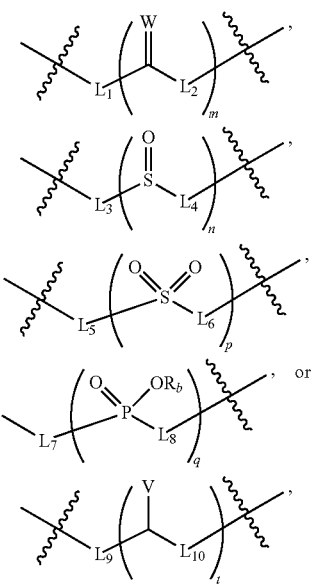

in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

18. The nanocomplex of claim 17, wherein A is

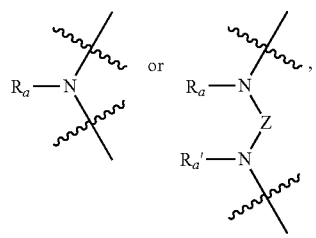

in which each of $R_a$ and $R_a'$, independently, is, H, a $C_1$-$C_{10}$ monovalent aliphatic radical, a $C_1$-$C_{10}$ monovalent heteroaliphatic radical, a monovalent aryl radical, or a monovalent heteroaryl radical; and Z is a $C_1$-$C_{10}$ bivalent aliphatic radical, a $C_1$-$C_{10}$ bivalent heteroaliphatic radical, a bivalent aryl radical, or a bivalent heteroaryl radical;

each of $B_1$ and $B_2$, independently, is a $C_{14\text{-}18}$ aliphatic radical or a $C_{14\text{-}18}$ heteroaliphatic radical; and each of $K_1$ and $K_2$, independently, is

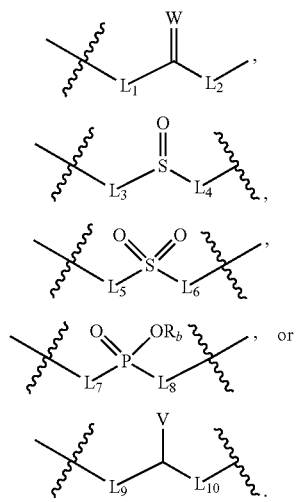

19. The nanocomplex of claim 18, wherein the lipid-like compound is

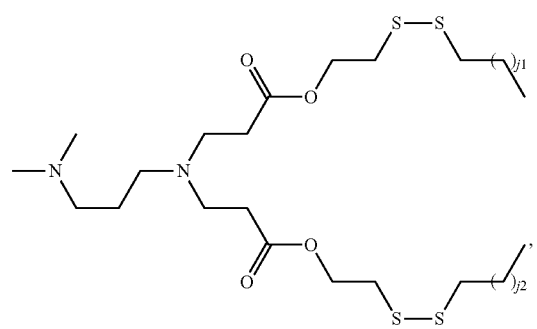

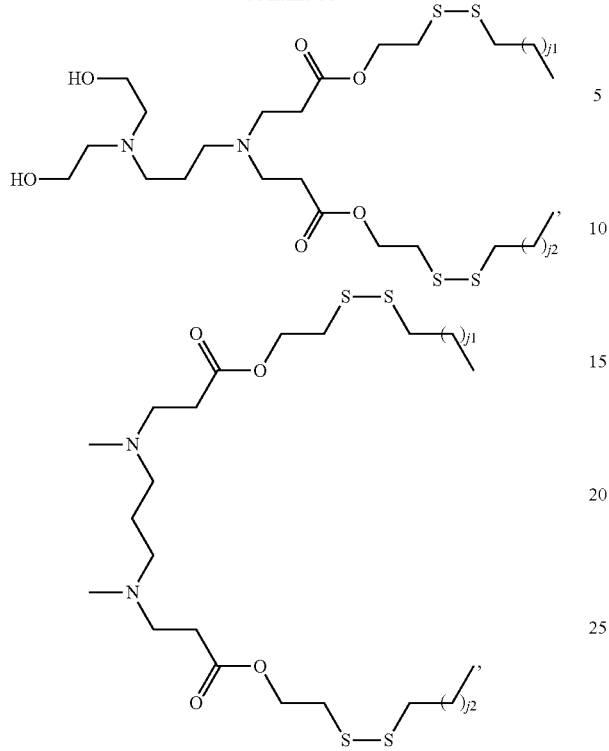

wherein each of j1 and j2 independently is 8, 9, 10, 11, or 12.

20. A pharmaceutical composition comprising a nanocomplex of claim 1; and a pharmaceutically acceptable carrier.

21. A method of treating a disease, comprising administering an effective amount of a nanocomplex of claim 1 to a patient in need thereof, wherein the disease is cancer, arthritis, neurodegenerative/cognitive disorders, an infection, chronic pain, or a sleeping disorder.

22. The method of claim 21, wherein the disease is cancer.

* * * * *